(12) United States Patent
Pilly et al.

(10) Patent No.: US 10,357,654 B1
(45) Date of Patent: *Jul. 23, 2019

(54) MAPPING TRANSCRANIAL SIGNALS TO TRANSCRANIAL STIMULATION REQUIRED TO REPRODUCE A BRAIN STATE

(71) Applicant: HRL Laboratories, LLC, Malibu, CA (US)

(72) Inventors: Praveen K. Pilly, West Hills, CA (US); Michael D. Howard, Westlake Village, CA (US)

(73) Assignee: HRL Laboratories, LLC, Malibu, CA (US)

( * ) Notice: Subject to any disclaimer, the term of this patent is extended or adjusted under 35 U.S.C. 154(b) by 146 days.

This patent is subject to a terminal disclaimer.

(21) Appl. No.: 15/338,118

(22) Filed: Oct. 28, 2016

Related U.S. Application Data

(63) Continuation-in-part of application No. 15/227,922, filed on Aug. 3, 2016, and a continuation-in-part of application No. 15/072,353, filed on Mar. 16, 2016.

(60) Provisional application No. 62/247,435, filed on Oct. 28, 2015, provisional application No. 62/210,890, filed on Aug. 27, 2015, provisional application No. 62/210,907, filed on Aug. 27, 2015.

(51) Int. Cl.
*A61N 1/36* (2006.01)
*A61B 5/0476* (2006.01)
*A61N 1/04* (2006.01)
*A61B 5/00* (2006.01)

(52) U.S. Cl.
CPC ........ *A61N 1/36025* (2013.01); *A61B 5/0476* (2013.01); *A61B 5/4836* (2013.01); *A61B 5/6803* (2013.01); *A61N 1/0456* (2013.01); *A61N 1/0484* (2013.01)

(58) Field of Classification Search
CPC .............. A61N 1/36025; A61N 1/3603; A61N 1/36031; A61N 1/36034; G06N 3/12; G06N 3/123; G06N 3/126
See application file for complete search history.

(56) References Cited

U.S. PATENT DOCUMENTS 8,718,778 B2   5/2014   Bikson et al.
9,116,835 B1   8/2015   Smyth
(Continued)

OTHER PUBLICATIONS

Fox, Peter T. et al. "Column-Based Model of Electric Field Excitation of Cerebral Cortex". Human Brain Mapping 22:1-16(2004).*
(Continued)

*Primary Examiner* — Allen Porter
(74) *Attorney, Agent, or Firm* — Tope-McKay & Associates

(57) ABSTRACT

Described is a system for computing a transcranial stimulation montage. The system obtains externally sensed brain activity representing a current brain state of a subject. Using the externally sensed brain activity, a desired brain activity change in each relevant voxel of the brain of the subject is translated into a necessary electrical field. A model the desired brain activity in relevant voxels of the brain of the subject is created. Using the model, an electrical stimulation montage is computed that can be applied by transcranial stimulation electrodes to a subject to transform the current brain state into a desired brain state.

18 Claims, 5 Drawing Sheets

(56) References Cited

U.S. PATENT DOCUMENTS

| | | |
|---|---|---|
| 9,370,658 B2 | 6/2016 | Neuvonen |
| 2009/0319002 A1 | 12/2009 | Simon |
| 2012/0046531 A1 | 2/2012 | Hua |
| 2012/0245653 A1 | 9/2012 | Bikson et al. |
| 2012/0265261 A1 | 10/2012 | Bikson |
| 2014/0057232 A1 | 2/2014 | Wetmore |
| 2015/0025590 A1 | 1/2015 | Cheng |
| 2016/0175589 A1 | 6/2016 | Wingeier |
| 2016/0228702 A1 | 8/2016 | Kempe |

OTHER PUBLICATIONS

Grech, R., Cassar, T., Muscat, J., Camilleri, K.P., Fabri, S.G., Zervakis, M., Xanthopoulos, P., Sakkalis, V. and Vanrumste, B., 2008. Review on solving the inverse problem in EEG source analysis. Journal of neuroengineering and rehabilitation, 5(1), pp. 1-33.

Tucker DM. Spatial sampling of head electrical fields: the geodesic sensor net. Electroencephalogr. Clin. Neurophysiol, 87: pp. 154-163, 1993.

Michel C., Murray MM. Towards the utilization of EEG as a brain imaging tool, NeuroImage 61 (2012), pp. 371-385.

Wolters CH, Anwander A, Tricoche X, Weinstein D, Koch MA, MacLeod RS. Influence of tissue conductivity anisotropy on EEG/MEG field and return current computation in a realistic head model: a simulation and visualization study using high-resolution finite element modeling. NeuroImage, 30: pp. 813-826, 2006.

Dmochowski JP, Datta A, Bikson M, Su Y, Parra LC. Optimized multi-electrode stimulation increases focality and intensity at target. J. Neural Eng., 8:046011, 2011, pp. 1-16.

Jones DK and Leemans A, "Diffusion Tensor Imaging", Methods in Molecular Biology 711: pp. 127-144, 2011.

Ramírez, Rey R., and Scott Makeig. "Neuroelectromagnetic source imaging of spatiotemporal brain dynamical patterns using frequency-domain independent vector analysis (IVA) and geodesic sparse Bayesian learning (gSBL)." In Proceedings of the 13th Annual Meeting of the Organization for Human Brain Mapping, Chicago, IL. 2007.

Nader K, Schafe GE, Le Doux JE. Fear memories require protein synthesis in the amygdala for reconsolidation after retrieval. Nature. 2000; 406: pp. 722-726.

Dudai Y. The neurobiology of consolidations, or, how stable is the engram? Annu. Rev. Psychol. 2004; 55: pp. 51-86.

Squire LR, Alvarez P. Retrograde amnesia and memory consolidation: a neurobiological perspective. Curr. Opin. Neurobiol. 1995; 5: pp. 169-177.

Foa EB. Social anxiety disorder treatments: psychosocial therapies. J. Clin. Psychiatry. 2006; 67 Suppl 12: pp. 27-30.

Seidler GH, Wagner FE. Comparing the efficacy of EMDR and trauma-focused cognitive-behavioral therapy in the treatment of PTSD: a meta-analytic study. Psychol. Med. 2006; 36: pp. 1515-1522.

Bustos SG, Maldonado H, Molina VA. Midazolam disrupts fear memory reconsolidation. Neuroscience. 2006; 139: pp. 831-842.

Sandrini M, Censor N, Mishoe J, Cohen LG. Causal Role of Prefrontal Cortex in Strengthening of Episodic Memories through Reconsolidation. Curr. Biol. 2013; 23: pp. 2181-2184.

Soterix Medical Website. High Definition-transcranial Direct Current Stimulation (HD-tDCS) [Internet]. Available from: http://soterixmedical.com/hd-tdcs, downloaded Aug. 8, 2016, pp. 1-13.

Chan JCK, LaPaglia JA. Impairing existing declarative memory in humans by disrupting reconsolidation. Proc. Natl. Acad. Sci. 2013;110: pp. 9309-9313.

Brunet A, Orr SP, Tremblay J, Robertson K, Nader K, Pitman RK. Effect of post-retrieval propranolol on psychophysiologic responding during subsequent script-driven traumatic imagery in post-traumatic stress disorder. J. Psychiatr. Res. 2008;42: pp. 503-506.

Euston DR, Gruber AJ, McNaughton BL. The role of medial prefrontal cortex in memory and decision making. Neuron. 2012; 76: pp. 1057-1070.

Ji D, Wilson MA. Coordinated memory replay in the visual cortex and hippocampus during sleep. Nat. Neurosci. 2007; 10: pp. 100-107.

Wolters CH, Anwander A, Tricoche X, Weinstein D, Koch MA, MacLeod RS. Influence of tissue conductivity anisotropy on EEG/MEG field and return current computation in a realistic head model: a simulation and visualization study using high-resolution finite element modeling. NeuroImage. 2006; 30: pp. 813-826.

Dmochowski JP, Datta A, Bikson M, Su Y, Parra LC. Optimized multi-electrode stimulation increases focality and intensity at target. J. Neural Eng. 2011; 8:pp. 046011-1-046011-16.

Edmund Rolls, "The mechanisms for pattern completion and pattern separation in the hippocampus," Front Syst Neurosci. Oct. 2013; vol. 7: Article 74, pp. 1-21.

Thomas J. McHugh, et al., "Dentate Gyrus NMDA Receptors Mediate Rapid Pattern Separation in the Hippocampal Network," Science, vol. 317, (Jul. 2007); pp. 94-99.

Jesse Rissman, et al., "Distributed representations in memory: Insights from functional brain imaging," Annu Rev Psychol. 2012 ; 63: pp. 101-128.

Giulio Ruffinia, et al., "Optimization of multifocal transcranial current stimulation for weighted cortical pattern targeting from realistic modeling of electric fields," Neuroimage. Apr. 1, 2014; 89: pp. 216-225.

Office Action 1 for U.S. Appl. No. 15/072,353, dated Oct. 19, 2016.

Tremblay, Sara, et al., "The uncertain outcome of prefrontal TDCS," Brain Stimulation 7.6 (2014): pp. 773-783. Web.

Segrave, R.A., et al., "concurrent cognitive control training augments the anidepressant efficacy of TDCS: A pilot study," Brain Stimulation 7.2 (2014): pp. 325-331. Web.

Castano-Candamil, Sebastian, et al., "Solving the EEG inverse problem based on space-time-frequency structured sparsity constraints," Neuroimage 118 (2015), pp. 598-612. Web.

Response to Office Action 1 for U.S. Appl. No. 15/072,353, dated Feb. 17, 2017.

McNamara CG, Tejero-Cantero A, Trouche S, Campo-Urriza N, Dupret D. Dopaminergic neurons promote hippocampal reactivation and spatial memory persistence. Nat Neurosci. 2014;17: pp. 1658-1660.

Marshall L, Helgadóttir H, Mölle M, Born J. Boosting slow oscillations during sleep potentiates memory. Nature. 2006;444: pp. 610-613.

Javadi AH, Walsh V. Transcranial direct current stimulation (tDCS) of the left dorsolateral prefrontal cortex modulates declarative memory. Brain Stimulat. 2012;5: pp. 231-241.

Rasch B, Büchel C, Gais S, Born J. Odor cues during slow-wave sleep prompt declarative memory consolidation. Science. 2007;315: pp. 1426-1429.

Rudoy JD, Voss JL, Westerberg CE, Paller KA. Strengthening Individual Memories by Reactivating Them During Sleep. Science. 2009;326: p. 1079.

Bendor D, Wilson MA. Biasing the content of hippocampal replay during sleep. Nat. Neurosci. 2012;15: pp. 1439-1444.

Abeyratne UR, Swarnkar V, Rathnayake SI, Hukins C. Sleep-stage and event dependency of brain asynchrony as manifested through surface EEG. Conf. Proc. Annu. Int. Conf. IEEE Eng. Med. Biol. Soc. IEEE Eng. Med. Biol. Soc. Conf. 2007;2007: pp. 709-712.

Salmi T, Brander PE. Computer assisted detection of REM and non-REM sleep for analysis of nocturnal hypoxaemia in patients with ventilatory impairment. Int. J. Clin. Monit. Comput. 1994;11: pp. 63-70.

Euston et al. Fast-Forward Playback of Recent Memory Sequences in Prefrontal Cortex During Sleep. Science. Nov. 2007; 318 (5853): pp. 1147-1150.

The SenseWear armband as a Sleep Detection Device [Internet]. [cited Nov. 23, 2014]. pp. 1-9. Available from: http://www.bodymedia.com/Professionals/Whitepapers/The-SenseWear-armband-as-a-Sleep-Detection-Device?whence=.

Office Action 2 for U.S. Appl. No. 15/072,353, dated Apr. 24, 2017.

(56) References Cited

OTHER PUBLICATIONS

"An automated pipeline for constructing personalized virtual brains from multimodal neuroimaging data," NeuroImage, vol. 117, Aug. 15, 2015, pp. 343-357.
Krause, M. R., Zanos, T. P., Csorba, B. A., Pilly, P. K., Choe, J., Phillips, M. E., Datta, A., and Pack, C. C. (2017). Transcranial direct current stimulation facilitates associative learning and alters functional connectivity in the primate brain. Current Biology, 27(3), pp. 3086-3096.
Response to Office Action 2 for U.S. Appl. No. 15/072,353, dated Aug. 22, 2017.
Office Action 3 for U.S. Appl. No. 15/072,353, dated Oct. 6, 2017.
Response to Office Action 3 for U.S. Appl. No. 15/072,353, dated Jan. 8, 2018.
Notice of Allowance for U.S. Appl. No. 15/072,353, dated Apr. 17, 2018.
Ruffini et al., Optimization of multifocal transcranial current stimulation for weighted cortical pattern targeting from realistic modeling of electric fields, Neuroimage, 89:216-25, 2014.
Rissman and Wagner, "Distributed Representations in Memory: Insights from Functional Brain Imaging," Annual Rev Psychol, 63: 101-128, 2012.
Rolls, "The Mechanisms for Pattern Completion and Pattern Separation in the Hippocampus," Frontiers in Systems Neuroscience, 7: 74, 2013.
McHugh et al, "Dentate Gyrus NMDA Receptors Mediate Rapid Pattern Separation in the Hippocampal Network," Science, 317(5834): 94-99, 2007.
Michael Schirner, et al., "An automated pipeline for constructing personalized virtual brains from multimodal neuroimaging data," NeuroImage, vol. 117, Aug. 15, 2015, pp. 343-357.
Office Action 1 for U.S. Appl. No. 15/227,922, dated Dec. 13, 2016.
Tremblay, Sara, et al. "The Uncertain Outcome of Prefrontal TDCS." Brain Stimulation 7.6 (2014): 773-83. Web.
Segrave, R.A. et al. "Concurrent Cognitive Control Training Augments the Antidepressant Efficacy of TDCS: A Pilot Study." Brain Stimulation 7.2 (2014): 325-31. Web.
Castano-Candamil, Ssebastian et al. "Solving the EEG Inverse Problem Based on Space-Time-Frequency Structured Sparsity Constraints." Neuroimage 118 (2015) 598-612. Web.
Marshall, L. "Transcranial Direct Current Stimulation during Sleep Improves Declarative Memory." Journal of Neuroscience 24.44 (2004): 9985-992. Web.
Javadi, Amir Homayoun, and Paul Cheng. "Transcranial Direct Current Stimulation (tDCS) Enhances Reconsolidation of Long-Term Memory." Brain Stimulation 6.4 (2013): 668-74. Web.
Sahlem, Gregory L., et al. "Oscillating Square Wave Transcranial Direct Current Stimulation (tDCS) Delivered During Slow Wave Sleep Does Not Improve Declarative Memory More Than Sham: A Randomized Sham Controlled Crossover Study." Brain Stimulation 8.3 (2015): 528-34. Web.
Barham, Michael P., Peter G. Enticott, Russell Conduit, and Jarrad A.g. Lum. "Transcranial Electrical Stimulation during Sleep Enhances Declarative (but Not Procedural) Memory Consolidation: Evidence from a Meta-analysis."Neuroscience & Biobehavioral Reviews 63 (2016): 65-77. Web.
Eggert, Torsten, Hans Dorn, Cornelia Sauter, Michael A. Nitsche, Malek Bajbouj, and Heidi Danker-Hopfe. "No Effects of Slow Oscillatory Transcranial Direct Current Stimulation (tDCS) on Sleep-Dependent Memory Consolidation in Healthy Elderly Subjects." Brain Stimulation 6.6 (2013): 938-45. Web.
Westerberg, Carmen E., Susan M. Florczak, Sandra Weintraub, M.-Marsel Mesulam, Lisa Marshall, Phyllis C. Zee, and Ken A. Paller. "Memory Improvement via Slow-oscillatory Stimulation during Sleep in Older Adults." Neurobiology of Aging 36.9 (2015): 2577-586. Web.
Response to Office Action 1 for U.S. Appl. No. 15/227,922, dated Mar. 13, 2017.
Office Action 2 for U.S. Appl. No. 15/227,922, dated Apr. 24, 2017.
Response to Office Action 2 for U.S. Appl. No. 15/227,922, dated Aug. 24, 2017.
Office Action 3 for U.S. Appl. No. 15/227,922, dated Sep. 29, 2017.
Response to Office Action 3 for U.S. Appl. No. 15/227,922, dated Jan. 29, 2018.
Notice of Allowance for U.S. Appl. No. 15/227,922, dated May 30, 2018.

\* cited by examiner

MAPPING TRANSCRANIAL SIGNALS TO TRANSCRANIAL STIMULATION REQUIRED TO REPRODUCE A BRAIN STATE

CROSS-REFERENCE TO RELATED APPLICATIONS

This is a Continuation-in-Part Application of U.S. Non-Provisional application Ser. No. 15/072,353, filed Mar. 16, 2016, entitled, "Transcranial Intervention to Weaken Traumatic Memories," which is a Non-Provisional Application of U.S. Provisional Patent Application No. 62/210,890 filed Aug. 27, 2015, entitled, "Transcranial Intervention to Weaken Traumatic Memories," the entirety of which are incorporated herein by reference. U.S. Non-Provisional application Ser. No. 15/072,353 is also a Non-Provisional Application of U.S. Provisional Patent Application No. 62/210,907 filed Aug. 27, 2015, entitled, "Method to Enhance Specific Memories with tCS During Slow-Wave Sleep," the entirety of which is incorporated herein by reference. U.S. Non-Provisional application Ser. No. 15/072,353 is also a Non-Provisional Application of U.S. Provisional Application No. 62/247,435, filed in the United States on Oct. 28, 2015, entitled, "Mapping Transcranial Signals to Transcranial Stimulation Required to Reproduce a Brain State," the entirety of which is incorporated herein by reference.

This is ALSO a Continuation-in-Part Application of U.S. Non-Provisional application Ser. No. 15/227,922, filed in the United States on Aug. 3, 2016, entitled, Method to Enhance Specific Memories with tCS During Slow-Wave Sleep", which is a Non-Provisional Application of U.S. Provisional Patent Application No. 62/210,907, filed in the United States on Aug. 27, 2015, entitled, "Method to Enhance Specific Memories with tCS During Slow-Wave Sleep," the entirety of which are incorporated herein by reference. U.S. Ser. No. 15/227,922 is also a Non-Provisional Application of U.S. Provisional Patent Application No. 62/210,890, filed in the United States on Aug. 27, 2015, entitled, "Transcranial Intervention to Weaken Traumatic Memories," the entirety of which is incorporated herein by reference. U.S. Ser. No. 15/227,922 is also a Non-Provisional Application of U.S. Provisional Application No. 62/247,435, filed in the United States on Oct. 28, 2015, entitled, "Mapping Transcranial Signals to Transcranial Stimulation Required to Reproduce a Brain State," the entirety of which is incorporated herein by reference.

This is ALSO a Non-Provisional patent application of 62/247,435, filed on Oct. 28, 2015, entitled, Mapping Transcranial Signals to Transcranial Stimulation Required to Reproduce a Brain State," the entirety of which is hereby incorporated by reference.

BACKGROUND OF INVENTION

(1) Field of Invention

The present invention relates to a system for computing a transcranial stimulation montage and, more particularly, to a system for computing a transcranial stimulation montage that reproduces a previously sensed brain state.

(2) Description of Related Art

External brain sensors, such as electroencephalogram (EEG), pick up signals from the scalp of a subject that indicate activity on the surface of the brain. It has long been recognized that EEGs can be analyzed to infer the activity in the three-dimensional (3D) volume of the brain that could have caused the particular surface signals sensed by the EEG using topographic maps and spatial pattern analysis methods as well as source localization techniques, as described in Literature Reference No. 1 of the List of Incorporated Literature References.

Non-invasive (i.e., transcranially applied) electrical stimulation of the brain has been shown in prior art to modulate neuronal activity and synchrony across multiple brain areas and enhance various behavioral functions. However, these demonstrations have been based upon coarse stimulation of areas of brain tissue without regard to the orientation of the neurons.

Existing methods to discover invasive and non-invasive stimulation patterns to enhance a particular behavioral function are essentially based on an expensive experimental process of trial and error. For example, if one has 8 scalp electrodes and 20 possible locations with 10 levels of intensity and 5 levels of frequency for non-invasive stimulation, then one would need 6,298,500 trials to determine the best stimulation montage for a subject in a brute-force way.

Thus, a continuing need exists for a method to compute a correct transcranial stimulation application such that no trial-and-error procedure is required while taking into account the dominant orientation of the neurons in each voxel of the brain volume, thus more accurately affecting a desired brain state.

SUMMARY OF INVENTION

The present invention relates to a system for computing a transcranial stimulation montage and, more particularly, to a system for computing a transcranial stimulation montage that reproduces a previously sensed brain state. The system comprises one or more processors and a memory having instructions such that when the instructions are executed, the one or more processors perform multiple operations. The system uses externally sensed brain activity representing a desired brain state and a current brain state to translate a desired brain activity change in each relevant voxel of the brain into a necessary electrical field. Application of an electrical stimulation montage by transcranial stimulation electrodes is controlled to transform the current brain state into the desired brain state, the electrical stimulation montage including the necessary electrical field.

In another aspect, a desired activity change in each relevant voxel is translated into the necessary electric field based on diffusion tensor imaging (DTI) data of white matter tract orientation in each relevant voxel.

In another aspect, the amount of current that is applied along an axis of neurons in the particular voxel is proportional to the amount of desired activity change.

In another aspect, G is a gain factor that is held constant during application of the electrical stimulation montage and $\Delta S$ is the desired activity change, and the amount of current that is applied along an axis of neurons in the particular voxel is $$I = \frac{\Delta S}{G}.$$

In another aspect, changes in brain activity after application of the electrical stimulation montage are measured, and the set of measured changes in brain activity are used to adjust a gain factor G for induced currents to affect brain activity change in each voxel.

In another aspect, gain factors G in each voxel are scaled by the cosine of an angle between a dominant white matter tract orientation and an induced electric field.

In another aspect, a model of the desired brain activity in relevant voxels of the brain is created.

Finally, the present invention also includes a computer program product and a computer implemented method. The computer program product includes computer-readable instructions stored on a non-transitory computer-readable medium that are executable by a computer having one or more processors, such that upon execution of the instructions, the one or more processors perform the operations listed herein. Alternatively, the computer implemented method includes an act of causing a computer to execute such instructions and perform the resulting operations.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

Figure 1:
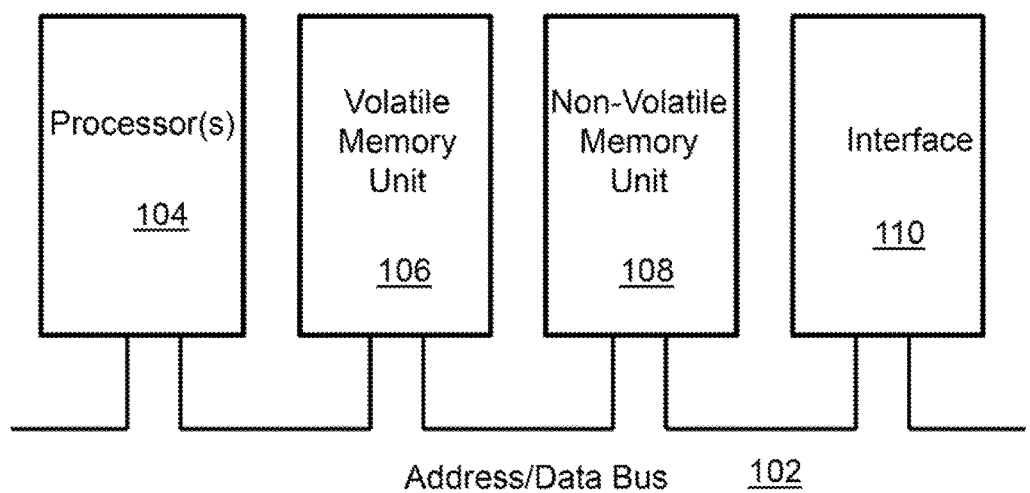
FIG. 1 is a block diagram depicting the components of a system for computing a transcranial stimulation montage according to embodiments of the present disclosure.
Figure 1:
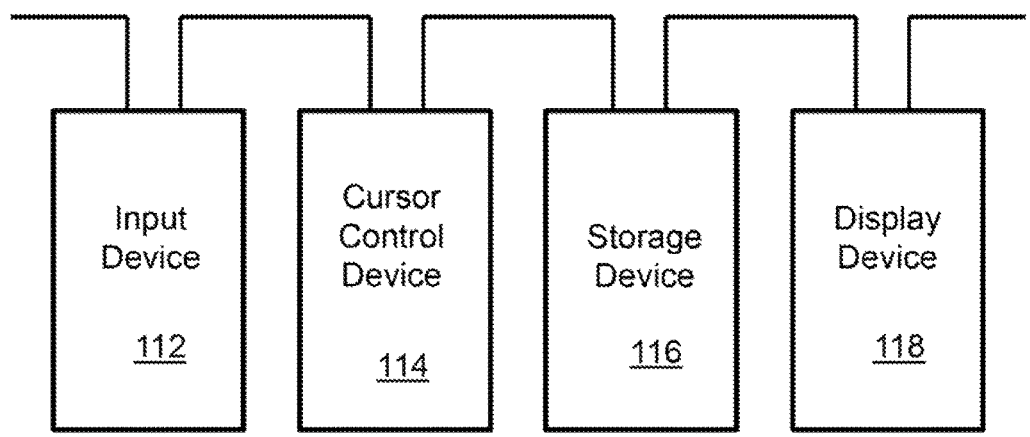

The present invention relates to a system for computing a transcranial stimulation montage and, more particularly, to a system for computing a transcranial stimulation montage that reproduces a previously sensed brain state.

The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of aspects. Thus, the present invention is not intended to be limited to the aspects presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Before describing the invention in detail, first a list of cited references is provided. Next, a description of the various principal aspects of the present invention is provided. Subsequently, an introduction provides the reader with a general understanding of the present invention. Finally, specific details of various embodiment of the present invention are provided to give an understanding of the specific aspects.

(1) LIST OF INCORPORATED LITERATURE REFERENCES

The following references are cited and incorporated throughout this application. For clarity and convenience, the references are listed herein as a central resource for the reader. The following references are hereby incorporated by reference as though fully set forth herein. The references are cited in the application by referring to the corresponding literature reference number, as follows:

1. Wong P. Introduction to Brain Topography. New York, N.Y., USA: Plenum Press, 1991.
2. Tucker D M. Spatial sampling of head electrical fields: the geodesic sensor net. Electroencephalogr. Clin. Neurophysiol, 87:154-63, 1993.
3. Michel C., Murray M M. Towards the utilization of EEG as a brain imaging tool. NeuroImage, 2012.
4. Wolters C H, Anwander A, Tricoche X, Weinstein D, Koch M A, MacLeod R S. Influence of tissue conductivity anisotropy on EEG/MEG field and return current computation in a realistic head model: a simulation and visualization study using high-resolution finite element modeling. NeuroImage, 30:813-26, 2006.
5. Dmochowski J P, Datta A, Bikson M, Su Y, Parra L C. Optimized multi-electrode stimulation increases focality and intensity at target. J. Neural Eng., 8:046011, 2011.
6. Ramirez R, Makeig S. Neuromagnetic source imaging of spatiotemporal brain dynamical patterns using frequency domain independent vector analysis (IVA) and geodesic sparse Bayesian learning (gSBL). Chicago, Ill.: Organization for Human Brain Mapping, 2007.
7. Jones D K and Leemans A, "Diffusion Tensor Imaging", Methods in Molecular Biology 711:127-144, 2011.

(2) PRINCIPAL ASPECTS

Various embodiments of the invention include three "principal" aspects. The first is a system for computing a transcranial stimulation montage. The system is typically in the form of a computer system operating software or in the form of a "hard-coded" instruction set. This system may be incorporated into a wide variety of devices that provide different functionalities. The second principal aspect is a method, typically in the form of software, operated using a data processing system (computer). The third principal aspect is a computer program product. The computer program product generally represents computer-readable instructions stored on a non-transitory computer-readable medium such as an optical storage device, e.g., a compact disc (CD) or digital versatile disc (DVD), or a magnetic storage device such as a floppy disk or magnetic tape. Other, non-limiting examples of computer-readable media include hard disks, read-only memory (ROM), and flash-type memories. These aspects will be described in more detail below.

A block diagram depicting an example of a system (i.e., computer system 100) of the present invention is provided in FIG. 1. The computer system 100 is configured to perform calculations, processes, operations, and/or functions associated with a program or algorithm. In one aspect, certain processes and steps discussed herein are realized as a series of instructions (e.g., software program) that reside within computer readable memory units and are executed by one or more processors of the computer system 100. When executed, the instructions cause the computer system 100 to perform specific actions and exhibit specific behavior, such as described herein.

The computer system 100 may include an address/data bus 102 that is configured to communicate information. Additionally, one or more data processing units, such as a processor 104 (or processors), are coupled with the address/data bus 102. The processor 104 is configured to process information and instructions. In an aspect, the processor 104 is a microprocessor. Alternatively, the processor 104 may be a different type of processor such as a parallel processor, application-specific integrated circuit (ASIC), programmable logic array (PLA), complex programmable logic device (CPLD), or a field programmable gate array (FPGA).

The computer system 100 is configured to utilize one or more data storage units. The computer system 100 may include a volatile memory unit 106 (e.g., random access memory ("RAM"), static RAM, dynamic RAM, etc.) coupled with the address/data bus 102, wherein a volatile memory unit 106 is configured to store information and instructions for the processor 104. The computer system 100 further may include a non-volatile memory unit 108 (e.g., read-only memory ("ROM"), programmable ROM ("PROM"), erasable programmable ROM ("EPROM"), electrically erasable programmable ROM "EEPROM"), flash memory, etc.) coupled with the address/data bus 102, wherein the non-volatile memory unit 108 is configured to store static information and instructions for the processor 104. Alternatively, the computer system 100 may execute instructions retrieved from an online data storage unit such as in "Cloud" computing. In an aspect, the computer system 100 also may include one or more interfaces, such as an interface 110, coupled with the address/data bus 102. The one or more interfaces are configured to enable the computer system 100 to interface with other electronic devices and computer systems. The communication interfaces implemented by the one or more interfaces may include wireline (e.g., serial cables, modems, network adaptors, etc.) and/or wireless (e.g., wireless modems, wireless network adaptors, etc.) communication technology.

In one aspect, the computer system 100 may include an input device 112 coupled with the address/data bus 102, wherein the input device 112 is configured to communicate information and command selections to the processor 100. In accordance with one aspect, the input device 112 is an alphanumeric input device, such as a keyboard, that may include alphanumeric and/or function keys. Alternatively, the input device 112 may be an input device other than an alphanumeric input device. In an aspect, the computer system 100 may include a cursor control device 114 coupled with the address/data bus 102, wherein the cursor control device 114 is configured to communicate user input information and/or command selections to the processor 100. In an aspect, the cursor control device 114 is implemented using a device such as a mouse, a track-ball, a track-pad, an optical tracking device, or a touch screen. The foregoing notwithstanding, in an aspect, the cursor control device 114 is directed and/or activated via input from the input device 112, such as in response to the use of special keys and key sequence commands associated with the input device 112. In an alternative aspect, the cursor control device 114 is configured to be directed or guided by voice commands.

In an aspect, the computer system 100 further may include one or more optional computer usable data storage devices, such as a storage device 116, coupled with the address/data bus 102. The storage device 116 is configured to store information and/or computer executable instructions. In one aspect, the storage device 116 is a storage device such as a magnetic or optical disk drive (e.g., hard disk drive ("HDD"), floppy diskette, compact disk read only memory ("CD-ROM"), digital versatile disk ("DVD")). Pursuant to one aspect, a display device 118 is coupled with the address/data bus 102, wherein the display device 118 is configured to display video and/or graphics. In an aspect, the display device 118 may include a cathode ray tube ("CRT"), liquid crystal display ("LCD"), field emission display ("FED"), plasma display, or any other display device suitable for displaying video and/or graphic images and alphanumeric characters recognizable to a user.

The computer system 100 presented herein is an example computing environment in accordance with an aspect. However, the non-limiting example of the computer system 100 is not strictly limited to being a computer system. For example, an aspect provides that the computer system 100 represents a type of data processing analysis that may be used in accordance with various aspects described herein. Moreover, other computing systems may also be implemented. Indeed, the spirit and scope of the present technology is not limited to any single data processing environment. Thus, in an aspect, one or more operations of various aspects of the present technology are controlled or implemented using computer-executable instructions, such as program modules, being executed by a computer. In one implementation, such program modules include routines, programs, objects, components and/or data structures that are configured to perform particular tasks or implement particular abstract data types. In addition, an aspect provides that one or more aspects of the present technology are implemented by utilizing one or more distributed computing environments, such as where tasks are performed by remote processing devices that are linked through a communications network, or such as where various program modules are located in both local and remote computer-storage media including memory-storage devices.

Figure 2:
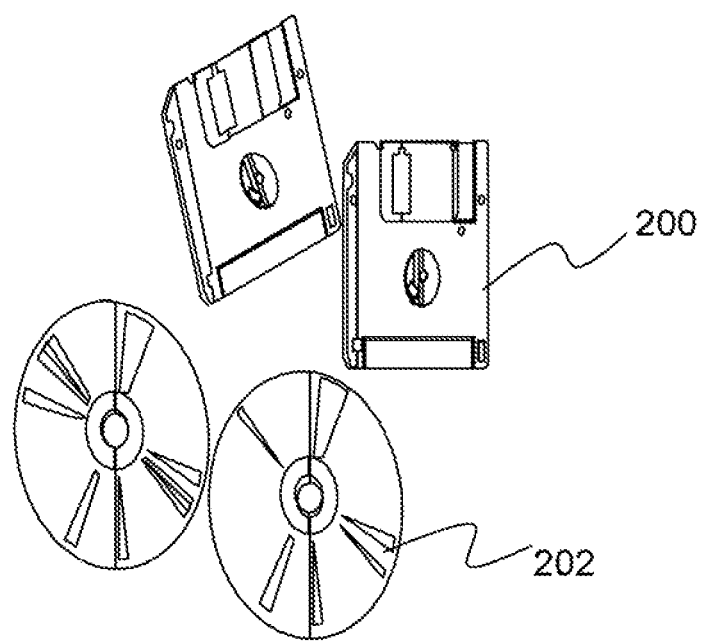
FIG. 2 is an illustration of a computer program product embodying an aspect of the present disclosure.

An illustrative diagram of a computer program product (i.e., storage device) embodying the present invention is depicted in FIG. 2. The computer program product is depicted as floppy disk 200 or an optical disk 202 such as a CD or DVD. However, as mentioned previously, the computer program product generally represents computer-readable instructions stored on any compatible non-transitory computer-readable medium. The term "instructions" as used with respect to this invention generally indicates a set of operations to be performed on a computer, and may represent pieces of a whole program or individual, separable, software modules. Non-limiting examples of "instruction" include computer program code (source or object code) and "hard-coded" electronics (i.e. computer operations coded into a computer chip). The "instruction" is stored on any non-transitory computer-readable medium, such as in the memory of a computer or on a floppy disk, a CD-ROM, and a flash drive. In either event, the instructions are encoded on a non-transitory computer-readable medium.

(3) INTRODUCTION

External brain sensors, such as electroencephalogram (EEG), receive signals from the scalp that indicate activity on the surface of the brain. It has long been recognized that the EEG can be analyzed to infer the activity in the three-dimensional (3D) volume of the brain that could have caused the particular surface signals sensed by EEG, using topographic maps and spatial pattern analysis methods as well as source localization techniques (see Literature Reference No. 1). Non-invasive (transcranially applied) electrical stimulation of the brain has been shown in prior art to modulate neuronal activity and synchrony across multiple brain areas and, thereby, to enhance various behaviors.

Described herein is a technique to compute a stimulation montage that can be applied by transcranial stimulation electrodes to reproduce a brain state that was previously sensed by EEG and/or functional near infrared sensing (fNIRS). This requires mapping the externally sensed signals to the most likely set of 3D sources of activity in the brain and then computing an electrical stimulation montage required to transform the current brain state into the desired brain state. The system according to embodiments of the present disclosure uses diffusion tensor imaging (DTI) data to link EEG sources with stimulation-induced current flows in the brain volume, which are different modalities. DTI provides average orientation and density of white matter tracts in each voxel, which are used to convert induced electric fields into neural activity changes. Each of these aspects will be described in further detail below.

(4) SPECIFIC DETAILS OF VARIOUS EMBODIMENTS

Based on T1- and T2-weighted magnetic resonance images (MRIs) of a human subject, finite element modeling is used to build a personalized forward model of voltage fluctuations recorded at the EEG/fNIRS electrodes on the scalp (as described in Literature Reference No. 4), as well as a personalized forward model of transcranial stimulation (tCS)-induced current density distributions in the brain volume (see Literature Reference No. 5 for a description of tCS-induced current density distributions). Multi-scale geodesic Sparse Bayesian Learning is used with a Laplacian prior for subject-specific inverse modeling to localize the distributed sources for the transcranially recorded EEG/fNIRS signals (see Literature Reference No. 6).

To determine the stimulation required to reproduce a particular activity pattern across the neocortex, the difference in activity for each voxel of the brain between the desired activity pattern and the current pattern was first computed. Based on diffusion tensor imaging (DTI) data of the subject, which provides fine-grained information on the white matter fiber orientation and density, one can compute the necessary electric field to achieve the desired activity change in each voxel. With the volumetric distribution of desired electric fields within the brain and the material properties of the scalp electrodes, as well as various tissue category masks in the brain volume, any of several types of optimization techniques can be employed to solve for the stimulation montage (such as the technique described in Literature Reference No. 5).

A point neuron activation function models the electrophysiological properties of real neurons, while simplifying their geometry to a single point. The neural activity S tends to increase linearly as a function of applied negative current I (i.e., the current out of a neuron, which moves negative charges away and increases positive potential). If one assumes the gain factor G stays constant during application of the stimulation, and the activity change desired in a particular voxel is $\Delta S$, then the amount of current that needs to be applied along the axis of the neurons in the voxel is $$I = \frac{\Delta S}{G}.$$

To determine the gain factors of various voxels for a given subject, one embodiment of the present disclosure is to arrive at them by applying various stimulation montages and measuring the corresponding affected activity changes across the brain volume. The gain factors in each voxel need to be scaled by the cosine of the angle between the dominant white matter tract orientation and the induced electric field. One skilled in the art can perform this procedure in a straightforward manner.

The procedure is summarized below. Steps 1-4 below create a model of desirable brain activity in the relevant voxels of the brain. This is a prerequisite to using the model to compute required brain stimulations to recreate a desired brain state. One example of a desired brain state is a state in which the subject's behavioral response to a certain experience is either enhanced or reduced. For instance, it could be beneficial to become more sensitive to threats of certain types. In the case of post-traumatic stress disorder, it is desirable to reduce anxiety triggered by certain benign events. Another non-limiting example is to enhance memory function in a person whose brain is improperly storing and recalling memories. In particular, step 2 must be done when the subject is in a desired brain state. For instance, in the case of post-traumatic stress disorder (PTSD), it is desirable to reduce anxiety triggered by certain benign events. Therefore, the desired brain state for a PTSD patient is one in which the subject is calm with low anxiety. Such a brain state can be achieved when the patient is in a quiet, safe place. Breathing exercises together with yoga or meditation are known to lower stress and may be used. Alternatively, calming videos such as the ones used by some airlines to settle passengers down before a long trip (e.g., wildlife scenes accompanied by relaxing music) may also be used.

1. Take T1- and T2-weighted MRIs and a DTI of the subject (as described in detail in Literature Reference No. 7).
2. During a desired brain state, record brain activity using EEG/fNIRS electrodes on the scalp.
3. Use finite element modeling based on the MRIs of step 1 to build a personalized forward model that describes how, for this subject, neural activity in the voxels of the brain create electrical signals that can be sensed on the surface of his skull, as described in Literature Reference No. 4.
4. Use multi-scale geodesic Sparse Bayesian Learning with a Laplacian prior for subject-specific inverse modeling to localize the distributed sources for the transcranially recorded (in step 2) EEG/fNIRS signals of the desired brain state, as described in Literature Reference No. 6. This provides desired activities in each voxel of the brain volume. In many cases, only a few brain regions are relevant for a particular use, the voxels can now be limited to a "relevant set".

5. Subsequently, once steps 1-4 are completed, and when the subject is in an undesirable brain state, record brain activity as in step 2.
6. Repeat step 4 for the undesired brain state.
7. Compute the difference in activity for each relevant voxel of the brain between the desired activity pattern and the current pattern.
8. Translate the desired activity change in each voxel into the necessary electric field, properly aligned to the orientation of the nerve fibers based on DTI data, to achieve the desired activity pattern.
9. With the volumetric distribution of desired electric fields within the brain, and the material properties of the scalp electrodes as well as various tissue category masks in the brain volume having been characterized, an optimization technique is employed to solve for the stimulation montage to create the desired activity change of step 8, analogous to beam-forming but imposing additional limits on the maximum injected current due to safety. In one embodiment, the optimization technique described in Literature Reference No. 5 is implemented. However, as can be appreciated by one skilled in the art, additional suitable methods exist that could be used to solve for the stimulation montage.
10. With the volumetric distribution of desired electric fields within the brain, and the material properties of the scalp electrodes as well as various tissue category masks in the brain volume having been characterized, any of several types of optimization techniques are employed to solve for the stimulation montage to create the desired activity change of step 8 (e.g., Literature Reference No. 5).
11. Apply the stimulation montage and repeat steps 5-9 as needed.

Figure 3:
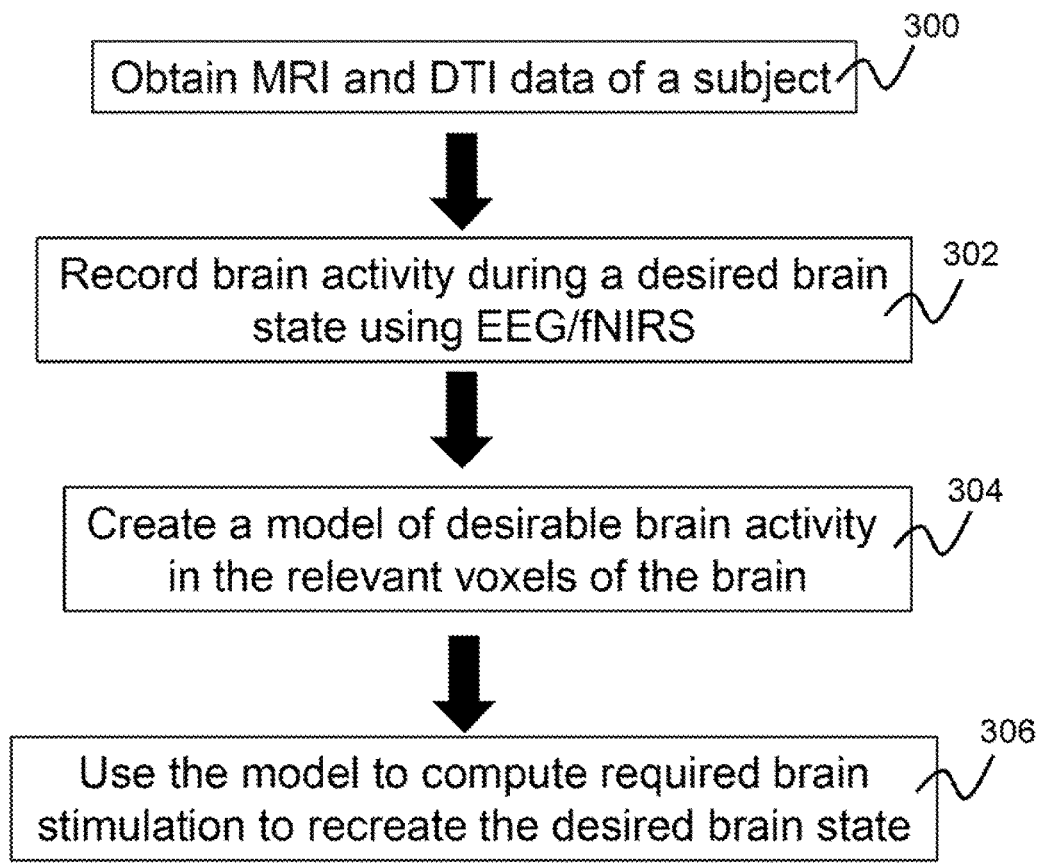
FIG. 3 is a flow diagram illustrating a method for computing a transcranial stimulation montage according to the embodiments of the present disclosure.

FIG. 3 is a flow diagram depicting the method described herein. As described above, the system obtains MRI and DTI data of a subject 300. Brain activity during a desired brain state is recorded using EEG/fNIRS 302. The system creates a model of desirable brain activity in the relevant voxels of the brain 304. The model is used to compute the required brain stimulation to recreate the desired brain state 306.

Figure 4:
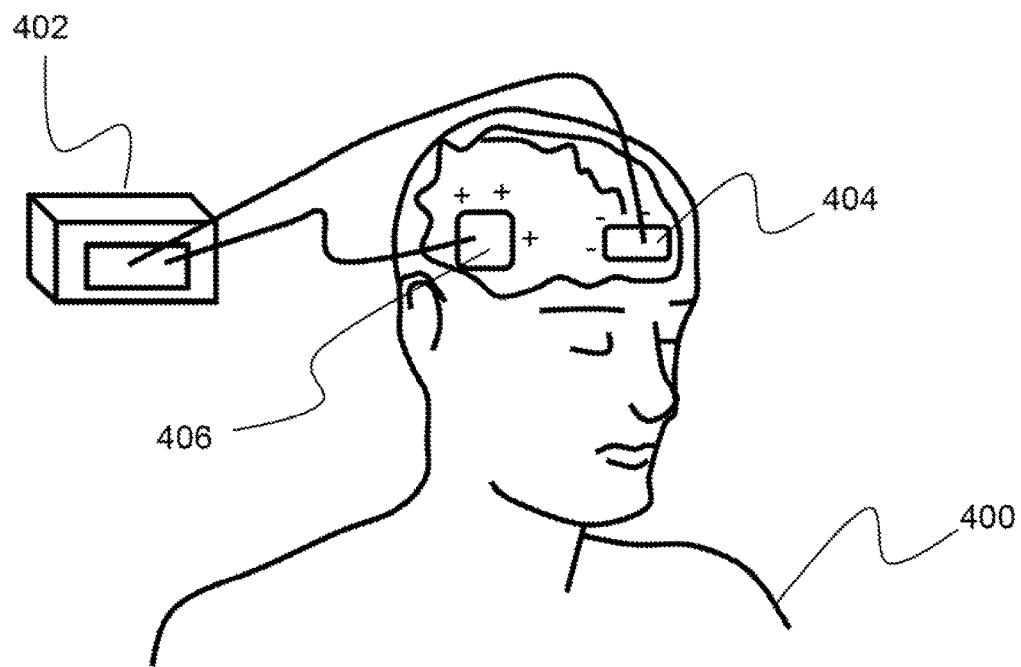
FIG. 4 illustrates a human subject receiving neurostimulation via a neural device according to some embodiments of the present disclosure.

FIG. 4 illustrates a human subject 400 receiving neurostimulation according to some embodiments of the present disclosure. A neural device 402 able to generate an electrical current delivers neurostimulation by applying a current through one electrode 404 (e.g., anode), and it flows through the brain to another electrode 406 (e.g., cathode). The neural device 402 is depicted as a patch that adheres to a portion of the patient's head. However, any suitable neural device 402 can be used (such as the neural cap described below) provided that it can control stimulation of specific neural regions based on a computed transcranial stimulation montage.

Figure 5:
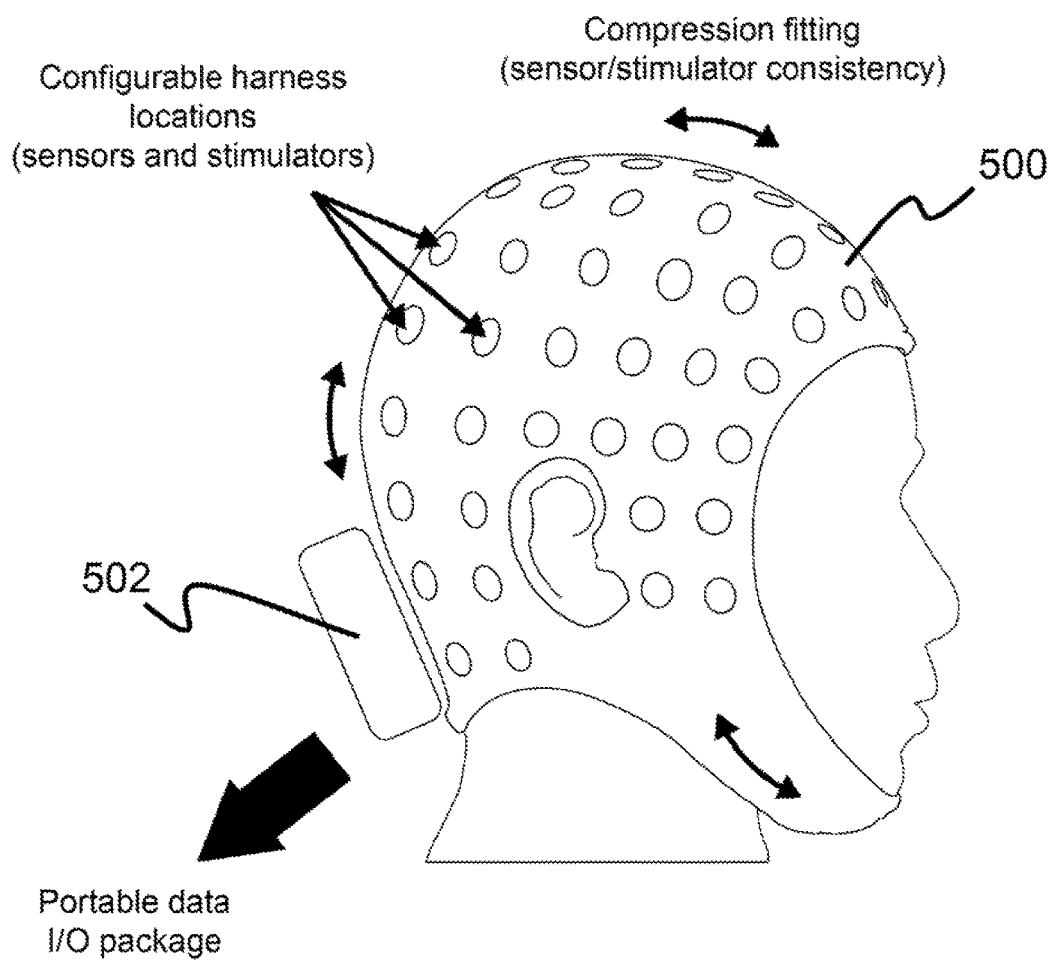
FIG. 5 illustrates a neural cap worn by a human subject for sensing and neurostimulation according to embodiments of the present disclosure.

FIG. 5 illustrates a neural device worn by a human subject for neurostimulation according to embodiments of the present disclosure. As depicted in FIG. 5, the neural device is a neural cap 500. As shown, the neural cap 500 may have configurable harness locations for stimulators and sensors. Compression fitting of the neural cap 500 achieves sensor/stimulator consistency. Furthermore, the neural cap 500 can be connected to portable data input/output (I/O) package 502.

There are many applications that can benefit from modifying brain states directly using safe non-invasive brain stimulation. For instance, researchers can develop a 'dictionary' of patterns associated with health and disease states—a project synergistic with international drives to map the human brain. The increasingly common use of high-density EEG systems with more than 100 electrodes (see Literature Reference No. 2), both in experimental and clinical settings, leads to an increasing request for such spatial analysis methods for the EEG as well (see Literature Reference No. 3).

In brain network circuits altered by disease, it is important to establish how introduced electrical impulses affect the disease and which patterns yield the most effective therapeutic responses. Developing the technology to modulate the activation of a larger set of central and peripheral neurons will be crucial to this pursuit. When one group of neurons is firing in a way that results in an undesirable overall brain state, and even disease, changing the neural activations so that they match the way they fire in a healthy or desirable state (using external electrical stimulation) causes learning to take place through spike timing-dependent plasticity, meaning that there are longer-term beneficial effects that last beyond the stimulation.

A non-invasive approach, such as the one described herein (in contrast to implanted electrodes), can potentially benefit 80% of patients with various behavioral deficits at less than 2% of the cost of implanting an electrode array, and without physical risk. In addition, a non-invasive approach avoids the drawbacks of implanted arrays, which have an average binary success rate of only 65% and require periodic new surgery to replace or reposition arrays, creating additional cost and risk. Furthermore, drug interventions can have undesirable systemic side effects.

The approach according to embodiments of the present disclosure will allow a personalized closed-loop system for affecting a desired distributed activity pattern in the brain by transcranially-applied electrical stimulation. The system described herein can be rapidly adopted by various practitioners of non-invasive stimulation for behavioral therapy. For instance, a commercial company MC10, Inc. located at 10 Maguire Road Building 3, $1^{st}$ Floor, Lexington, Mass. 02421, develops virtually invisible, conformal, and stretchable electronic sensors that adhere to the skin. Innovations such as this, including an active "tattoo" on the head that would both sense and adapt brain states, will only increase the potential commercial applications of the technology described herein.

Finally, while this invention has been described in terms of several embodiments, one of ordinary skill in the art will readily recognize that the invention may have other applications in other environments. It should be noted that many embodiments and implementations are possible. Further, the following claims are in no way intended to limit the scope of the present invention to the specific embodiments described above. In addition, any recitation of "means for" is intended to evoke a means-plus-function reading of an element and a claim, whereas, any elements that do not specifically use the recitation "means for", are not intended to be read as means-plus-function elements, even if the claim otherwise includes the word "means". Further, while particular method steps have been recited in a particular order, the method steps may occur in any desired order and fall within the scope of the present invention.

What is claimed is:

1. A system for computing a transcranial stimulation montage, the system comprising:
one or more processors and a memory, the memory being a non-transitory computer-readable medium having executable instructions encoded thereon, such that upon execution of the instructions, the one or more processors perform operations of:
mapping externally sensed brain activity data representing a first brain state to voxels of brain volume;
mapping externally sensed brain activity data representing a second brain state to voxels of brain volume;
translating a brain activity change from the second brain state to the first brain state in each relevant voxel of the brain into a necessary electrical field based on diffusion tensor imaging (DTI) data,
wherein the DTI imaging data provides an average white matter tract orientation in each relevant voxel, and wherein the translated brain activity change in each relevant voxel is translated into the necessary electrical field by aligning to the average white matter tract orientation in each relevant voxel;
computing an electrical stimulation montage from the translated brain activity change; and
controlling application of the electrical stimulation montage by transcranial stimulation electrodes to transform the second brain state into the first brain state, the electrical stimulation montage including the necessary electrical field.

2. The system as set forth in claim 1, wherein the amount of current that is applied along an axis of neurons in the particular voxel is proportional to the amount of brain activity change.

3. The system as set forth in claim 2, wherein G is a gain factor that is held constant during application of the electrical stimulation montage and ΔS is the brain activity change, and the amount of current that is applied along an axis of neurons in the particular voxel is $$I = \frac{\Delta S}{G}.$$

4. The system as set forth in claim 1, wherein the one or more processors further perform operations of:
measuring changes in brain activity after application of the electrical stimulation montage; and
using the set of measured changes in brain activity, adjusting a gain factor G for induced currents to affect brain activity change in each voxel.

5. The system as set forth in claim 4, wherein gain factors G in each voxel are scaled by the cosine of an angle between a dominant white matter tract orientation and an induced electric field.

6. The system as set forth in claim 1, wherein the one or more processors further perform an operation of creating a model of the brain activity representing the first brain state in relevant voxels of the brain.

7. A computer program product for computing a transcranial stimulation montage, the computer program product comprising:
a non-transitory computer-readable medium having executable instructions encoded thereon, such that upon execution of the instructions by one or more processors, the one or more processors perform operations of:
mapping externally sensed brain activity data representing a first brain state to voxels of brain volume;
mapping externally sensed brain activity data representing a second brain state to voxels of brain volume;
translating a brain activity change from the second brain state to the first brain state in each relevant voxel of the brain into a necessary electrical field using based on diffusion tensor imaging (DTI) data,
wherein the DTI imaging data provides an average white matter tract orientation in each relevant voxel, and wherein the translated brain activity change in each relevant voxel is translated into the necessary electrical field by aligning to the average white matter tract orientation in each relevant voxel;
computing an electrical stimulation montage from the translated brain activity change; and
controlling application of the electrical stimulation montage by transcranial stimulation electrodes to transform the second brain state into the first brain state, the electrical stimulation montage including the necessary electrical field.

8. The computer program product as set forth in claim 7, wherein the amount of current that is applied along an axis of neurons in the particular voxel is proportional to the amount of brain activity change.

9. The computer program product as set forth in claim 8, wherein G is a gain factor that is held constant during application of the electrical stimulation montage and ΔS is the brain activity change, and the amount of current that is applied along an axis of neurons in the particular voxel is $$I = \frac{\Delta S}{G}.$$

10. The computer program product as set forth in claim 7, further comprising instructions for causing the one or more processors to further perform operations of:
measuring changes in brain activity after application of the electrical stimulation montage; and
using the set of measured changes in brain activity, adjusting a gain factor G for induced currents to affect brain activity change in each voxel.

11. The computer program product as set forth in claim 10, wherein gain factors G in each voxel are scaled by the cosine of an angle between a dominant white matter tract orientation and an induced electric field.

12. The computer program product as set forth in claim 7, further comprising instructions for causing the one or more processors to further perform an operation of creating a model of the brain activity representing the first brain state in relevant voxels of the brain.

13. A computer implemented method for computing a transcranial stimulation montage, the method comprising an act of:
causing one or more processors to execute instructions encoded on a non-transitory computer-readable medium, such that upon execution, the one or more processors perform operations of:
mapping externally sensed brain activity data representing a first brain state to voxels of brain volume;

mapping externally sensed brain activity data representing a second brain state to voxels of brain volume;

translating a brain activity change from the second brain state to the first brain state in each relevant voxel of the brain into a necessary electrical field based on diffusion tensor imaging (DTI) data, wherein the DTI imaging data provides an average white matter tract orientation in each relevant voxel, and wherein the translated brain activity change in each relevant voxel is translated into the necessary electrical field by aligning to the average white matter tract orientation in each relevant voxel;

computing an electrical stimulation montage from the translated brain activity change; and controlling application of the electrical stimulation montage by transcranial stimulation electrodes to transform the second brain state into the first brain state, the electrical stimulation montage including the necessary electrical field.

14. The method as set forth in claim 13, wherein the amount of current that is applied along an axis of neurons in the particular voxel is proportional to the amount of brain activity change.

15. The method as set forth in claim 14, wherein G is a gain factor that is held constant during application of the electrical stimulation montage and ΔS is the brain activity change, and the amount of current that is applied along an axis of neurons in the particular voxel is $$I = \frac{\Delta S}{G}.$$

16. The method as set forth in claim 13, wherein the one or more processors further perform operations of:
  measuring changes in brain activity after application of the electrical stimulation montage; and
  using the set of measured changes in brain activity, adjusting a gain factor G for induced currents to affect brain activity change in each voxel.

17. The method as set forth in claim 16, wherein gain factors G in each voxel are scaled by the cosine of an angle between a dominant white matter tract orientation and an induced electric field.

18. The method as set forth in claim 13, wherein the one or more processors further perform an operation of creating a model of the brain activity representing the first brain state in relevant voxels of the brain.

* * * * *